United States Patent
Walker (10) Patent No.: US 10,501,698 B1
(45) Date of Patent: Dec. 10, 2019

(54) COUNTERCURRENT AND CROSS CURRENT HIGH PRESSURE EXTRACTION TECHNIQUES FOR BIODIESEL FUEL

(71) Applicant: James Cameron Walker, Bradenton, FL (US)

(72) Inventor: James Cameron Walker, Bradenton, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/782,178

(22) Filed: Oct. 12, 2017

Related U.S. Application Data (60) Provisional application No. 62/407,102, filed on Oct. 12, 2016.

(51) Int. Cl.
| | | |
|---|---|---|
| C10L 1/00 | (2006.01) |
| C07C 1/22 | (2006.01) |
| C07C 7/10 | (2006.01) |
| C10L 1/02 | (2006.01) |
| C11B 3/00 | (2006.01) |

(52) U.S. Cl.
CPC .............. C10L 1/026 (2013.01); C11B 3/006 (2013.01); *C10L 2290/544* (2013.01)

(58) Field of Classification Search
CPC combination set(s) only.
See application file for complete search history.

(56) References Cited

U.S. PATENT DOCUMENTS

| | | |
|---|---|---|
| 2005/0188607 A1 | 9/2005 | Lastella |
| 2012/0277461 A1 | 11/2012 | Roa-Espinosa et al. |
| 2016/0186066 A1* | 6/2016 | Powell ............... C10G 1/002 585/242 |

FOREIGN PATENT DOCUMENTS

| | | |
|---|---|---|
| CN | 103159590 A | 6/2013 |
| WO | 2012004489 A1 | 1/2012 |

OTHER PUBLICATIONS

Cao et al., Methanol recycling in the production of biodiesel in a membrane reactor, Fuel 87, 825-833, 2008.

(Continued)

*Primary Examiner* — Ellen M McAvoy
*Assistant Examiner* — Chantel L Graham
(74) *Attorney, Agent, or Firm* — Thomas|Horstemeyer, LLP (57) ABSTRACT

Methods of extracting biodiesel from a mixture of biodiesel and alcohol are provided. The methods can include contacting the mixture of biodiesel and alcohol with a petrodiesel to form a two-phase system including a polar phase and a nonpolar phase, wherein the alcohol preferentially partitions into the polar phase and the petrodiesel and biodiesel preferentially partition into the nonpolar phase, and separating the nonpolar phase from the polar phase to extract the biodiesel. The methods can include using a multi-stage extraction apparatus, for example in countercurrent or cross-current extraction arrangement. Methods of making a biodiesel blend are also provided. The methods can include making a biodiesel blend with a biodiesel content from about B2 to about B25.

13 Claims, 8 Drawing Sheets

(56) References Cited

OTHER PUBLICATIONS

De Souse Maia et al., Liquid-Liquid Equilibrium of Methyl Esters of Fatty Acid / Methanol / Glycerol and Fatty Acid Ethyl Esters / Ethanol / Glycerol: A Case Study for Biodiesel Application, International Journal of Chemical Engineering and Applications, vol. 4, No. 5, 285-289, 2013.

Lim et al., Influences of different co-solvents in simultaneous supercritical extraction and transesterification of Jatropha curcas L. seeds for the production of biodiesel, Chemical Engineering Journal 221, 436-445, 2013.

* cited by examiner

COUNTERCURRENT AND CROSS CURRENT HIGH PRESSURE EXTRACTION TECHNIQUES FOR BIODIESEL FUEL

CROSS-REFERENCE TO RELATED APPLICATIONS

This application claims priority to, and the benefit of, U.S. provisional application entitled "COUNTERCURRENT AND CROSS CURRENT HIGH PRESSURE EXTRACTION TECHNIQUES FOR BIODIESEL FUEL" having Ser. No. 62/407,102, filed Oct. 12, 2016, the contents of which are incorporated by reference in their entirety.

TECHNICAL FIELD

The present disclosure generally relates to methods of biodiesel extraction and biodiesel production.

BACKGROUND

Biodiesel production in the United States amounted to 105 million gallons in January of 2016 alone. Most of this fuel, however, is not used by consumers in its pure form. Commercial vehicles only infrequently possess engines rated for B100 (that is, 100% biodiesel) consumption. The market for biodiesel is constrained by the percentage of biodiesel for which popular engines are rated. Most commercial and personal vehicles are rated for between 2 and 20 volume percent of biodiesel fuel, with the remainder composed of petrodiesel. The task of producing this blend presently falls to vendors or customers further down the product lifecycle.

Due to these limitations, biodiesel is typically adulterated with conventional petrodiesel to produce dilutions as low as B2. These dilutions are most commonly achieved by simple splash blending, wherein purified B100 and petrodiesel are mixed by the convective motion of pouring both fuels into an on-site vessel. This method has the advantage of simplicity, but suffers from a lack of elegance and efficiency. Splash blending frequently results in incompletely mixed fuel, reducing consumer confidence in biofuel performance. Mechanically agitating large volumes of fluid is expensive, particularly if handled by retail-level vendors that may not be able to justify the price of such an operation. Methods such as in-line blending (injection of B100 into the diesel line servicing a fueling station) has problems with ASTM quality control, as the blend itself is not testable until it is exiting the fuel hose.

Non-catalytic supercritical processes of biodiesel production have become popular because they can handle high water and free fatty acid content. The supercritical conditions of high temperature and pressure be used to catalyze the transesterification reaction. At a high temperature and pressure, methanol and other small alcohols enter a supercritical region. In the supercritical region, the alcohol behaves like a compressible fluid having density intermediate between that of a gas and that of a liquid. Viscosity and surface tension of supercritical methanol is low, allowing excellent mass transfer characteristics. However, the high pressure and high methanol concentration processes of biodiesel production face the problem of energy loss associated with current product purification strategies.

There remains a need for improved methods of separating biodiesel and of making biodiesel blends that overcome the aforementioned deficiencies.

SUMMARY

A variety of methods are provided herein capable of overcoming the aforementioned deficiencies. In various embodiments, the methods can be used to separate biodiesel from a mixture of biodiesel and alcohol using a petrodiesel extraction solvent. Under the right thermodynamic conditions described herein, biodiesel, alcohol, and petrodiesel form a two-phase liquid system having a polar phase and a nonpolar phase, wherein the alcohol preferentially partitions into the polar phase, and the biodiesel and petrodiesel preferentially partition into the nonpolar phase. In various aspects, the methods can be performed at temperatures and pressures used in supercritical biodiesel production. This feature, coupled with the ability to use petrodiesel as an extraction solvent, can allow for the simultaneous production of a range of biodiesel blends. The methods can include countercurrent extraction of the biodiesel from the mixture using a multi-stage extraction apparatus and a petrodiesel solvent. The methods can include crosscurrent extraction of the biodiesel from the mixture using a multi-stage extraction apparatus and a petrodiesel solvent.

If the temperature or pressure are at the conditions of the reactor effluent, the supercritical alcohol will simply dissolve the conventional diesel too. Controlling temperature, pressure and petrodiesel influent allows for the generation of the desired two-phase equilibrium. For methanol, the aforementioned equilibrium, across a range of operating pressures and temperatures, includes a liquid phase of nearly pure methanol and a liquid phase of approximately 35% petrodiesel, 5% biodiesel, and 60% methanol. Following repeated countercurrent extraction, the methanol in the product stream can be reduced from a 42:1 ratio to the product to a 5:1 ratio. This trace methanol can be flashed off with little effort and fed into the makeup stream.

In various embodiments, methods of extracting biodiesel from a mixture of biodiesel and alcohol are provided. The methods can include contacting the mixture of biodiesel and alcohol with a petrodiesel to form a two-phase system including a polar phase and a nonpolar phase, wherein the alcohol preferentially partitions into the polar phase and the petrodiesel and biodiesel preferentially partition into the nonpolar phase. The methods can include separating the nonpolar phase from the polar phase to extract the biodiesel.

In various embodiments, methods of extracting biodiesel from a mixture of biodiesel and alcohol using a multi-stage extraction apparatus are provided. The methods can include pumping the mixture into a first stage of a multi-stage extraction apparatus. The methods can include pumping a petrodiesel into a last stage of the multi-stage extraction apparatus. The methods can include removing a polar phase from the last stage of the multi-stage extraction apparatus, wherein the polar phase comprises the alcohol. The methods can include removing a nonpolar phase from the first stage of the multi-stage extraction apparatus, wherein the nonpolar phase comprises the petrodiesel and the biodiesel.

In a variety of embodiments, the methods include crosscurrent extraction methods using a multi-stage extraction apparatus having a plurality of stages configured in a crosscurrent extraction arrangement. The methods can include pumping petrodiesel into each of the stages, wherein a two-phase system is formed in each stage, wherein the two-phase system includes a polar phase and a nonpolar phase. In various aspects, the alcohol preferentially partitions into the polar phase and the petrodiesel and biodiesel preferentially partition into the nonpolar phase in each stage. The methods can include pumping the polar phase from each stage and into a next stage until exiting the last stage, i.e. the polar phase from the first stage is pumped into the second stage, the polar phase from the second stage is pumped into the third stage, until the polar phase is finally removed from the last stage. The methods can include removing the nonpolar phase from each stage to extract the biodiesel. The nonpolar phase from each stage can include a mixture of the biodiesel and the petrodiesel, wherein the concentration of the biodiesel in the nonpolar phase leaving each stage decreases from the first stage to the last stage.

In a variety of embodiments, the methods include countercurrent extraction methods using a multi-stage extraction apparatus having a plurality of stages configured in a countercurrent extraction arrangement. The methods can include pumping the mixture into a first stage of a multi-stage extraction apparatus, and pumping a petrodiesel into a last stage of the multi-stage extraction apparatus. A two-phase system can be formed in each stage, wherein the two-phase system includes a polar phase and a nonpolar phase. In various aspects, the alcohol preferentially partitions into the polar phase and the petrodiesel and biodiesel preferentially partition into the nonpolar phase in each stage. The methods can include pumping the polar phase from each stage and into a next stage until exiting the last stage. The methods also include pumping the nonpolar phase from each stage and into a preceding stage until exiting from the first stage to extract the biodiesel.

A variety of multi-stage extraction apparatuses can be used in the methods described herein, including a variety of stages and a variety of volumetric flow rates. In various aspects, the multi-stage extraction apparatus has from 4 to 12 stages. In some aspects, the methods can include operating at a pressure of about 80 bar to 140 bar. The methods can include applying a pressure differential across each of the stages in the multi-stage apparatus, e.g. a pressure difference of about 0.5 bar to about 5 bar can be applied across each stage. The methods can be applied at a variety of temperatures, e.g. in some embodiments the temperature is about 20° C. to about 100° C. The alcohol can include a variety of small alcohols commonly used in biodiesel production, including methanol, ethanol, 1-propanol, 2-propanol, and a combination thereof. In some embodiments, the alcohol is methanol or a mixture of methanol and other alcohols.

The methods provided herein can be used to separate biodiesel from a biodiesel and alcohol mixture in a variety of situations. In some embodiments, the concentration of biodiesel in the mixture prior to the separation is about 2 mol % to about 20 mol %. In some embodiments, the mixture is the product from a supercritical biodiesel production. The methods can be used to separate the biodiesel so that the alcohol can be reused, e.g. can be regenerated back into the biodiesel production. In some embodiments, when the biodiesel is extracted in a nonpolar phase during the extraction, the concentration of the biodiesel extracted in the nonpolar phase is about 5 mol % to about 30 mol % after the extraction. In some embodiments, essentially all of the biodiesel is removed from the alcohol mixture using multi-stage extraction. For example, in some aspects the concentration of the biodiesel in the alcohol is about 500 ppm or less after the extraction.

Provided herein are methods that can include integration of the blending process with the fuel production process. Petrodiesel is primarily composed of nonpolar molecules such as long-chain alkanes, aromatics and cyclic alkanes. The weak polarity of methanol allows it to dissolve the locally-polar biodiesel molecules, but the strongly nonpolar petrodiesel is a far more effective biodiesel solvent. In various embodiments, methods of making a biodiesel blend are provided, the method can include extracting biodiesel from a mixture of biodiesel and alcohol using a multi-stage extraction method provided herein, wherein the biodiesel blend has a biodiesel content from about B2 to about B25.

This leaves the plant with about 90% of the recycled methanol still at 90 bar and a product that can be sold at retail price by the plant to consumers or at wholesale price to vendors as a B15 biofuel blend. With petrodiesel on hand for the extraction process, this product can also be further diluted to B2 to access a wider market of approved engine types.

Other systems, methods, features, and advantages of the methods and systems for biodiesel processing will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
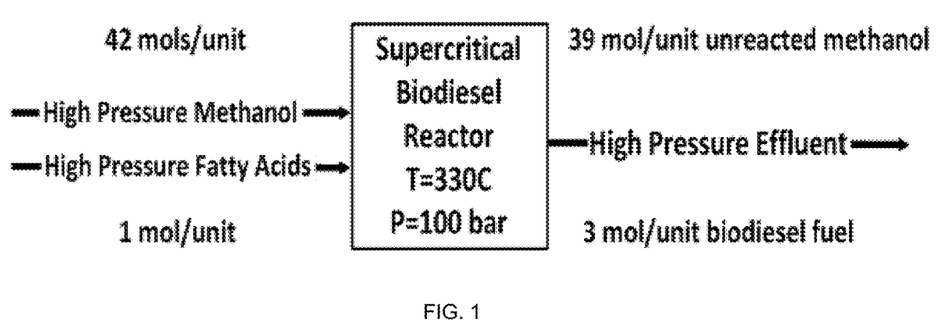
FIG. 1 is a diagram depicting a supercritical biodiesel process where the high pressure effluent exits the reactor as a single product stream after reacting the two inlet streams.
Figure 2:
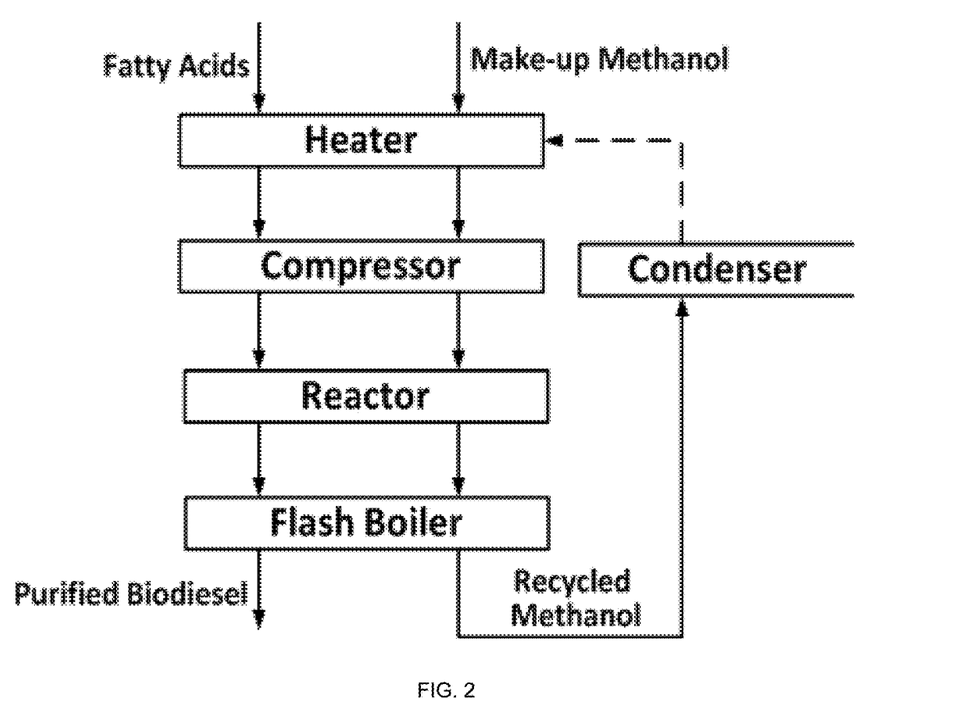
FIG. 2 is a flow diagram of the conventional process for removing methanol from the biodiesel in a high pressure effluent stream with methanol recycling.

An emerging technique in the biodiesel processing industry is the supercritical reaction pathway. This particular reaction is carried out in excel alcohol, typically excess methanol under supercritical conditions. FIG. 1 shows the high pressure effluent that exiting the reactor as a single product stream after reacting the two inlet streams. In order to use the biodiesel as fuel, the remaining alcohol must be removed from the high pressure effluent. The conventional procedure for this purification process is outlined in FIG. 2.

The recycle of the alcohol is important for environmental and financial reasons. Many of the small alcohols used, such as methanol, are water soluble and toxic to humans, and therefore must be either disposed of safely or burned, the latter of which adds to the lifecycle carbon footprint of biodiesel production. Moreover, the reuse of methanol or other alcohols is an effective way to reduce operating cost in supercritical biodiesel plants, which, as an emerging technology, may be faced with narrow profit margins.

Figure 3:
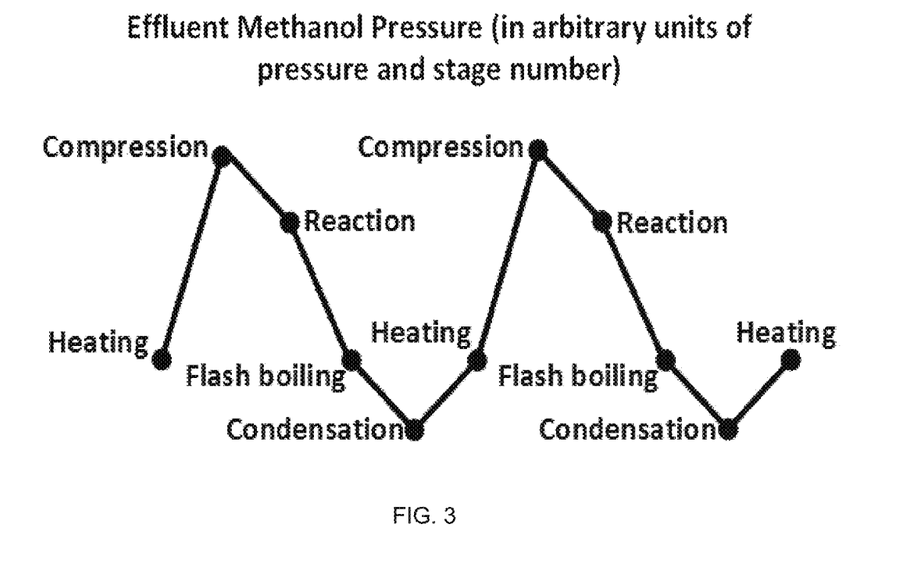
FIG. 3 is a graph depicting the pressure (in arbitrary pressure units) of methanol as it goes through two cycles of the process depicted in FIG. 2.

Associated with the recycling is the need to change the pressure of the alcohol to separate it from the biodiesel fuel. In conventional approaches, flash boiling or distillation is used to evaporate the alcohol. For example, the methanol can only be boiled without supplying additional heat at a pressure of around 5 bar. Once evaporated, it must be condensed and recompressed in order to use it again. The compressor must supply enough power to bring the recycled methanol back to at least 100 bar in a conventional supercritical biodiesel production. FIG. 3 follows the pressure of a given mol of methanol through two cycles of the conventional process, assuming that it was not reacted. The increases in pressure represent energy input into the system, either by elevating the temperature or reducing the volume of the alcohol. Repeatedly recompressing the alcohol from 5 to 100 bar is necessarily a sustained energy load on the biodiesel plant operation. This is the present form of supercritical biodiesel production.

Provided herein are methods that can alleviate this energy load by reducing pressure changes in the alcohol recycle stream. The methods can include keeping the alcohol, such as methanol, in the liquid phase during the separation process, avoiding the steps of evaporation and condensation. The methods can include a high-pressure liquid-liquid extraction of the biodiesel from the alcohol using petrodiesel.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "percent by weight," as used herein, refers to the amount of a component in a blend or mixture. In general this refers to grams of a component per 100 grams of a mixture. For example a mixture having "10% compound X by weight" refers to 10 grams of compound X in 100 grams of the mixture. Unless otherwise indicated, any percentages stated herein are percent by weight.

The term "biodiesel," as used herein, refers to a fuel derived from vegetable oil or animal fat. In general, a biodiesel is composed of primarily fatty acid alkyl esters.

The terms "petroleum diesel" and "petrodiesel," as used interchangeably herein, refer to a petroleum middle distillate fuel, such as grade No. 1 or grade No. 2 diesel as defined by the specifications outlined by ASTM D975 in the United States or similar EN 590 specifications in Europe.

The term "biodiesel blend," as used herein, refers to a fuel that is a blend of a biodiesel and another fuel. In general, biodiesels are blended with a petroleum-based fuel (i.e., "petrodiesel"). Biodiesel blends are referred to as BXX. The "XX" indicates the amount of biodiesel in the blend. B100 is 100% biodiesel or "neat" biodiesel. A B20 blend, for example, is a 20% volumetric blend of biodiesel with 80% petrodiesel.

The phrase "mixture of fatty acids" or "blend of fatty acids" or "fatty acid blend" may be used interchangeably and refer to a composition that includes various fatty acids. In certain embodiments a mixture of fatty acids can be an oil or blend of oils, in other embodiments a mixture of fatty acids can be a mixture of free fatty acids or a mixture of free fatty acids and an oil or blend of oils. In certain embodiments some or all of the fatty acids in a mixture of fatty acids can be modified to form fatty acid alkyl esters, for example fatty acid methyl esters, fatty acid ethyl esters, fatty acid propyl esters and the like. In certain preferred embodiments, the fatty acid alkyl esters include methyl esters.

The term "oil," as used herein, refers to a substance composed primarily of triglycerides of fatty acids. Vegetable oils can be extracted from various parts of the plant, including the seeds, fruit, or leaves of plants. Vegetable oils are generally liquid at room temperatures. In some embodiments the oils are derived from canola, rapeseed, palm, palm kernel, coconut, tucum, sunflower, safflower, olive, macadamia, babassu, castor, peanut, cotton, flaxseed, linseed, cohune, and jatropha. In further embodiments, the oils can be derived from a genetically modified plant.

Fatty acids contain carbon, hydrogen, and oxygen arranged as a carbon chain skeleton with a carboxyl group at one end. Fatty acids may be saturated fatty acids (SFAs) and have no carbon-carbon double bonds, monounsaturated (MUFAs) and have one carbon-carbon double bond, or poly unsaturated fatty acids (PUFAs) and have more than one carbon-carbon double bond. The number of carbons in a fatty acid chain and the number of carbon-carbon double bonds is commonly expressed as "number of carbons: number of carbon-carbon double bonds." For example, oleic acid, which has 18 carbons and one double bond, can be expressed as "O18:1" or "18:1."

"Medium chain fatty acids," as used herein, refers to fatty acids containing 6 to 14 carbons, preferably 8 to 12 carbons.

"Long chain fatty acids," as used herein, refers to fatty acids containing more than 14 carbons, or more that 16 carbons, or even more than 18 carbons.

"Feedstock" as used herein refers to a substance composed of fats, fatty acids, or triglycerides that may be used as a starting material for the preparation of a biodiesel. Examples of feedstocks which may be used in the production of biodiesels include vegetable oil, Waste vegetable oil, and animal fats. Other feedstocks include mixtures of fatty acids or fatty acid alkyl esters.

Biodiesel and Methods of Making Biodiesel

A variety of methods for biodiesel production have been demonstrated, including homogenous base catalysts, homogeneous acid catalysts, solid-state heterogeneous catalysts, and supercritical.

Supercritical Process

Non-catalytic supercritical processes of biodiesel production can handle high water and free fatty acid content. At a high temperature and pressure, methanol enters a supercritical region. In the supercritical region, it behaves like a compressible fluid having density intermediate between that of a gas and that of a liquid. Viscosity and surface tension of supercritical methanol is low, allowing excellent mass transfer characteristics. An increase in temperature decreases the ionic product of various polar solvents such as $CO_2$, alcohols, and water. Supercritical biodiesel production can be accomplished with a variety of alcohols, including methanol, ethanol, 1-propanol, 2-propanol, 1-butanol, 2-ethoxyethanol, and a combination thereof.

The transesterification reaction between triglycerides and supercritical alcohol can take place without any catalyst present. The hydrogen bonding between the alcohol molecules decreases dramatically in the supercritical region, allowing alcohol molecules to act as an acid catalyst. At high pressure, the alcohol monomer directly attacks the triglyceride carbonyl atom and imparts a positive charge. The methoxide is transferred and the intermediate dissociates forming a fatty acid alkyl ester molecule and a diglyceride molecule. This sequence is repeated twice more until glycerol is formed as an end product.

High temperatures are preferable for saturated fatty acids and that they show faster and more complete conversion when the temperatures are high. However, as temperatures increase, unsaturated fatty acids can tend to degrade. Hence, temperatures are generally kept below 550° C.

Pressure is known to affect the physical properties of supercritical alcohol. At high pressure, fluid density is also high, allowing more collisions between alcohols, such as methanol molecules, and oil. The collisions create better contact and increase reaction rates. Various alcohols have different critical conditions. Further, the addition of carbon atoms changes the polarity and hydrogen bonding, among other physico-chemical properties. The temperature requirements can also be higher for longer alcohols because the critical temperature is higher for longer alcohols.

In various aspects, the oil used for biodiesel production can include soybean oil, palm oil, coconut oil, or a combination thereof. In various aspects, the oils are largely mixtures of triglycerides (over 90%) and fatty acids. They vary in terms of the number of carbon atoms they have and their degree of saturation, which can result in adjustments in reaction conditions and minor variations in ester properties.

Biodiesel Blends and Methods of Biodiesel Extraction

Methods are provided for extracting biodiesel from a mixture containing biodiesel and alcohol. Liquid-liquid extraction is the practice of adding a chemical to a mixture to create two distinct liquid phases. The methods herein select a solvent that will dissolve biodiesel but remain insoluble in the methanol. A solvent that creates a second liquid phase with a new concentration of feedstock components is called a mass separating agent. The solubility characteristics of alcohols, such as methanol, and biodiesel, which are functions of system temperature and pressure, are carefully selected for the methods described herein.

Figure 4:
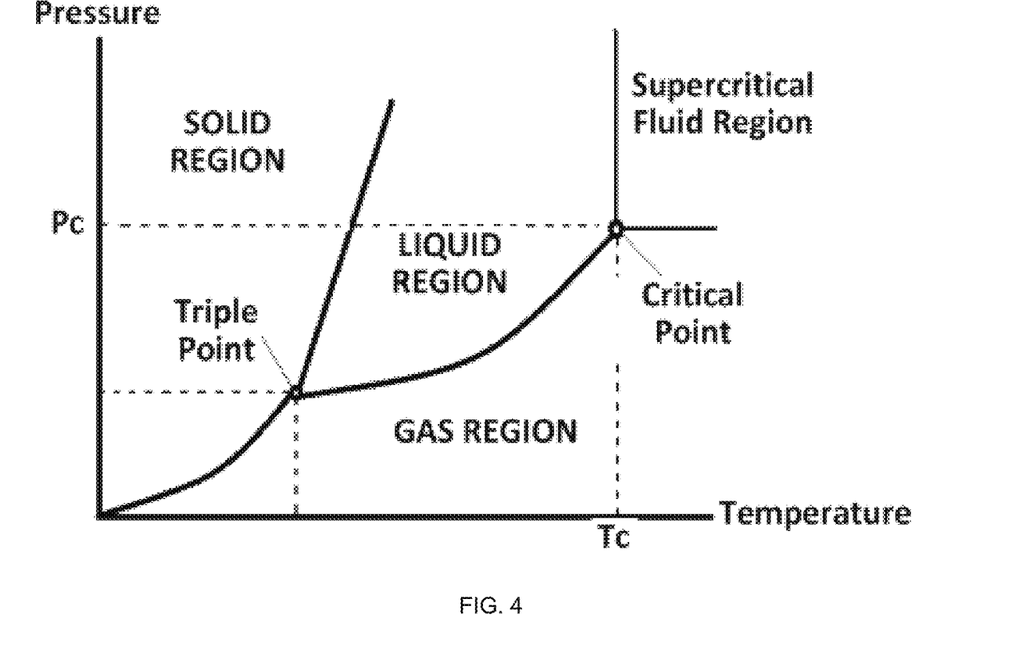
FIG. 4 is an exemplary phase diagram of a fluid

At supercritical conditions, the alcohols such as methanol have a nonpolar character due to quantum effects. Below this supercritical state, the methanol has a weakly polar behavior, while the biodiesel has a weakly nonpolar behavior. Above the critical point, by definition, there is a single supercritical phase, while slightly below it, entropic mixing effects exceed the intermolecular forces required to induce phase separation. This condition results in a single liquid phase. FIG. 4 shows a generic phase diagram for a near-critical fluid. Moving to the left (decreasing in temperature) will produce this condition. It is then necessary to introduce a mass separating agent to create a separable second liquid phase. A strongly nonpolar solvent will dissolve the biodiesel more effectively than it will dissolve the small alcohols such as methanol.

In various embodiments, the methods can be used to separate biodiesel from a mixture of biodiesel and alcohol using a petrodiesel extraction solvent. Under the right thermodynamic conditions described herein, biodiesel, alcohol, and petrodiesel form a two-phase liquid system having a polar phase and a nonpolar phase, wherein the alcohol preferentially partitions into the polar phase, and the biodiesel and petrodiesel preferentially partition into the nonpolar phase. In various aspects, the methods can be performed at temperatures and pressures used in supercritical biodiesel production. This feature, coupled with the ability to use petrodiesel as an extraction solvent, can allow for the simultaneous production of a range of biodiesel blends. The methods can include countercurrent extraction of the biodiesel from the mixture using a multi-stage extraction apparatus and a petrodiesel solvent. The methods can include crosscurrent extraction of the biodiesel from the mixture using a multi-stage extraction apparatus and a petrodiesel solvent.

Under the right thermodynamic conditions, biodiesel, alcohol, and petrodiesel form a two-phase liquid system. If the temperature or pressure are at the conditions of the reactor effluent, the supercritical alcohol will simply dissolve the conventional diesel too. Controlling temperature, pressure and petrodiesel influent allows for the generation of the desired two-phase equilibrium. For methanol, the aforementioned equilibrium, across a range of operating pressures and temperatures, includes a liquid phase of nearly pure methanol and a liquid phase of approximately 35% petrodiesel, 5% biodiesel, and 60% methanol. Following repeated countercurrent extraction, the methanol in the product stream can be reduced from a 42:1 ratio to the product to a 5:1 ratio. This trace methanol can be flashed off with little effort and fed into the makeup stream.

The methods can include contacting the mixture of biodiesel and alcohol with a petrodiesel to form a two-phase system including a polar phase and a nonpolar phase, wherein the alcohol preferentially partitions into the polar phase and the petrodiesel and biodiesel preferentially partition into the nonpolar phase. The methods can include separating the nonpolar phase from the polar phase to extract the biodiesel.

The methods can include pumping the mixture into a first stage of a multi-stage extraction apparatus. The methods can include pumping a petrodiesel into a last stage of the multi-stage extraction apparatus. The methods can include removing a polar phase from the last stage of the multi-stage extraction apparatus, wherein the polar phase comprises the alcohol. The methods can include removing a nonpolar phase from the first stage of the multi-stage extraction apparatus, wherein the nonpolar phase comprises the petrodiesel and the biodiesel.

In a variety of embodiments, the methods include crosscurrent extraction methods using a multi-stage extraction apparatus having a plurality of stages configured in a crosscurrent extraction arrangement. The methods can include pumping petrodiesel into each of the stages, wherein a two-phase system is formed in each stage, wherein the two-phase system includes a polar phase and a nonpolar phase. In various aspects, the alcohol preferentially partitions into the polar phase and the petrodiesel and biodiesel preferentially partition into the nonpolar phase in each stage. The methods can include pumping the polar phase from each stage and into a next stage until exiting the last stage, i.e. the polar phase from the first stage is pumped into the second stage, the polar phase from the second stage is pumped into the third stage, until the polar phase is finally removed from the last stage. The methods can include removing the nonpolar phase from each stage to extract the biodiesel. The nonpolar phase from each stage can include a mixture of the biodiesel and the petrodiesel, wherein the concentration of the biodiesel in the nonpolar phase leaving each stage decreases from the first stage to the last stage.

In a variety of embodiments, the methods include countercurrent extraction methods using a multi-stage extraction apparatus having a plurality of stages configured in a countercurrent extraction arrangement. The methods can include pumping the mixture into a first stage of a multi-stage extraction apparatus, and pumping a petrodiesel into a last stage of the multi-stage extraction apparatus. A two-phase system can be formed in each stage, wherein the two-phase system includes a polar phase and a nonpolar phase. In various aspects, the alcohol preferentially partitions into the polar phase and the petrodiesel and biodiesel preferentially partition into the nonpolar phase in each stage. The methods can include pumping the polar phase from each stage and into a next stage until exiting the last stage. The methods can also include pumping the nonpolar phase from each stage and into a preceding stage until exiting from the first stage to extract the biodiesel.

Biodiesel fuel is very rarely used in pure form. Most commonly, it is adulterated to produce mixtures containing between 80% and 98% conventional diesel by volume. These mixtures are referred to as being between B20 and B2; generalized, a BX grade of biodiesel is X % biodiesel by volume.

Figure 5:
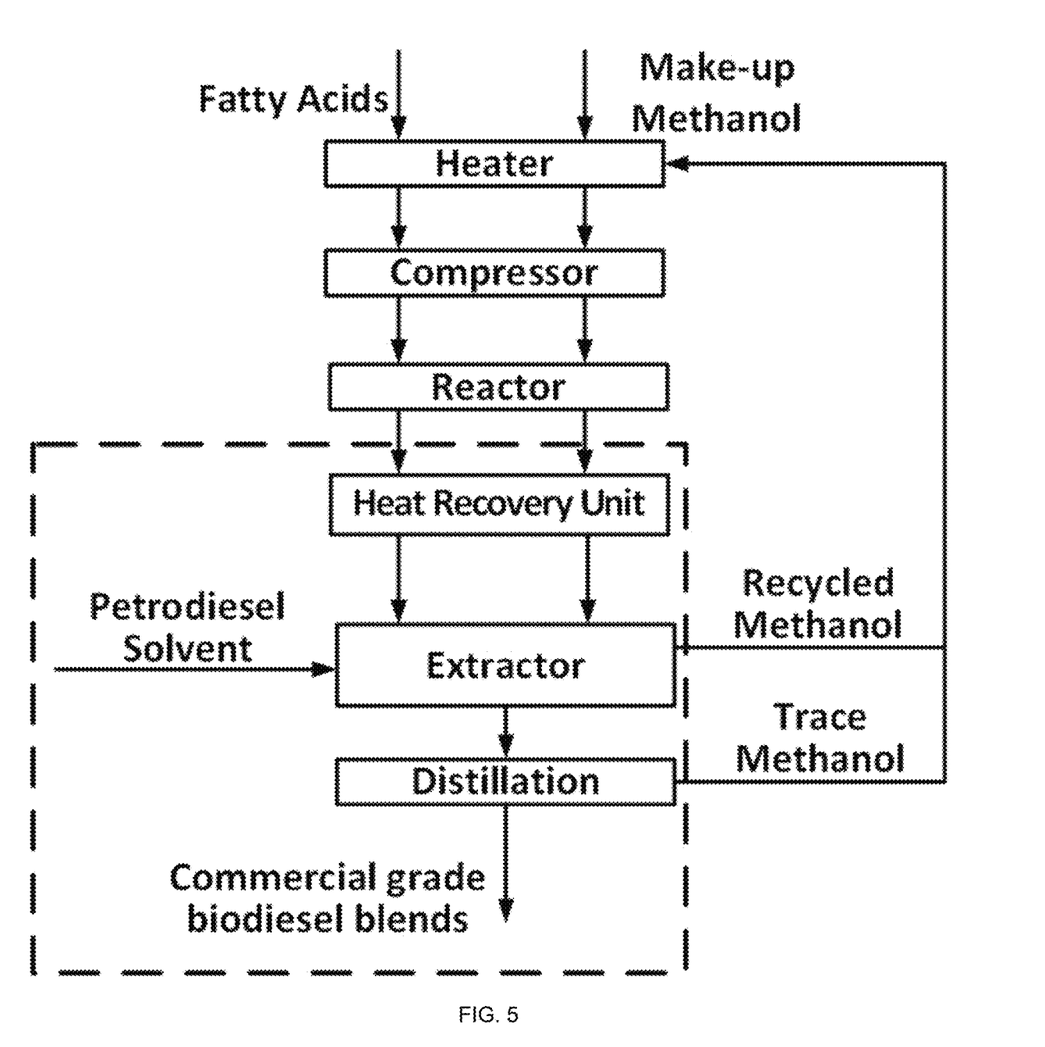
FIG. 5 is a flow diagram of an exemplary embodiment demonstrating a process for biodiesel extraction using petrodiesel as an extraction solvent with methanol recycling.

It so happens that conventional diesel fuel (henceforth referred to as petrodiesel) is strongly nonpolar. This is convenient because it is a solvent for biodiesel that does not have to be removed. This is an advantage over traditional liquid-liquid extraction, where the extracted product must typically be removed from the solvent in an additional step. For this reason, it is desirable to seek a way to use petrodiesel as a mass separating agent. Thus, the methods described herein include a process that integrates biodiesel blending with biodiesel purification. The simplified flowchart in FIG. 5 demonstrates the process. The black box highlights the technology added to the process by this invention.

Figure 6:
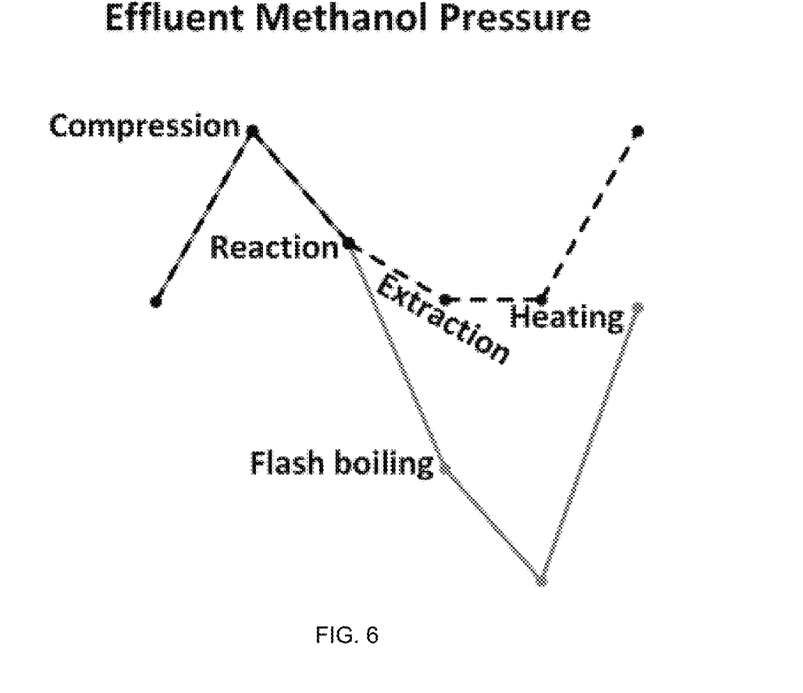
FIG. 6 is a graph depicting the pressure (in arbitrary pressure units) of methanol as it goes through one cycle of the conventional process (solid lines, depicted in FIG. 2) and as it goes through the exemplary process of biodiesel extraction using petrodiesel (dashed lines, depicted in FIG. 5).

The high-pressure extraction methods can be used for producing various biodiesel blends. The methods benefit from the elimination of the downstream step of producing a biodiesel blend by moving it from vendors and customers to the actual production pathway. Additionally, large pressure gradients between process steps are significantly reduced, decreasing the load on pumps and compressors in the system by minimizing differential pressures. In FIG. 6, the pressure pathway of high-pressure biodiesel extraction is compared to the pressure pathway of conventional methanol boiling.

Figure 8:
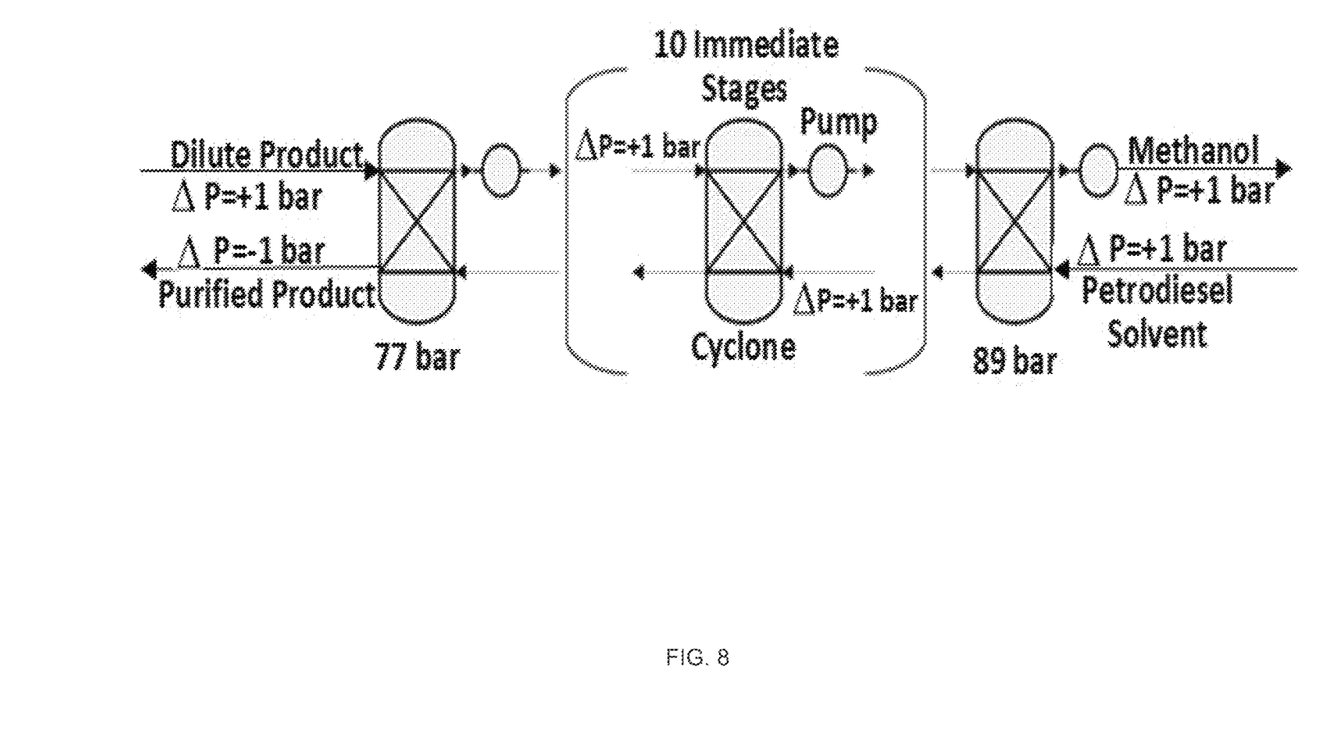
FIG. 8 is a diagram of the pump-cyclone battery layout.
Figure 9:
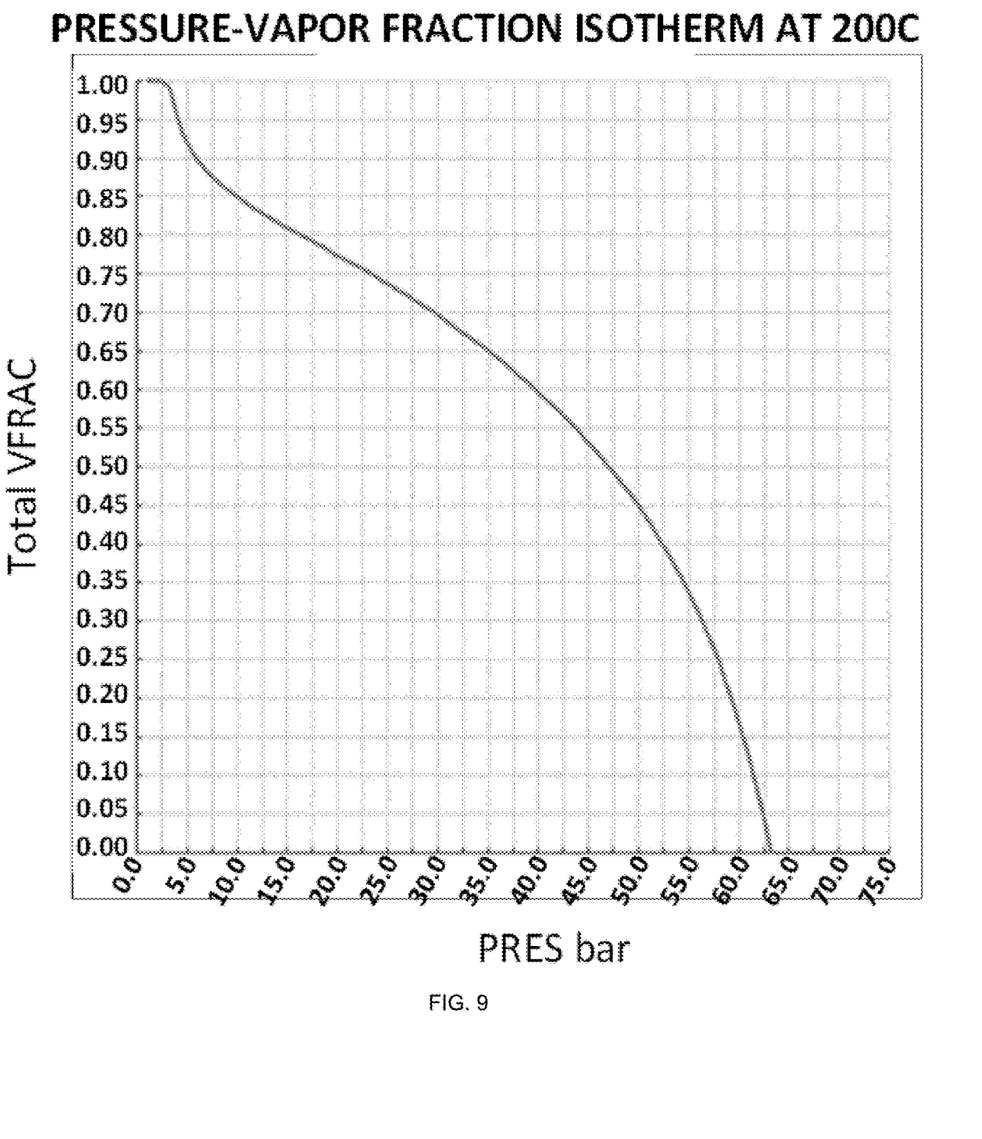
FIG. 9 is a pressure-vapor isotherm at 200° C. showing mol fraction of vapor for methanol.

A variety of multi-stage extraction apparatuses can be used in the methods described herein, including a variety of stages and a variety of volumetric flow rates. In some aspects, the apparatus includes a pump-cyclone battery layout as depicted in FIG. 8. In various aspects, the multi-stage extraction apparatus has from 4 to 12 stages. In some aspects, the methods can include operating at a pressure of about 80 bar to 140 bar. The methods can include applying a pressure differential across each of the stages in the multi-stage apparatus, e.g. a pressure difference of about 0.5 bar to about 5 bar can be applied across each stage. The methods can be applied at a variety of temperatures, e.g. in some embodiments the temperature is about 250° C. to about 350° C. The alcohol can include a variety of small alcohols commonly used in biodiesel production, including methanol, ethanol, 1-propanol, 2-propanol, 1-butanol, 2-ethoxyethanol, and a combination thereof. In some embodiments, the alcohol is methanol or a mixture of methanol and other alcohols.

The mechanical aspect of the extraction unit itself is also important to implementing this process. In order to drive the solvent and process streams in countercurrent, inter-stage (within the extractor; effectively sub-stages within the extraction stage) pumps will be required to direct fluid flow. A thermodynamic lower limit on the number of stages can be about 8 stages, about 9 stages, about 10 stages, about 11 stages, or about 12 stages.

A wide range of extractors are available; while ins some embodiments there are advantages to using an integrated mixing-settling unit in the form of a hydrocyclone, which themselves generate differential pressure that can be used to help drive the streams. Basic process control elements for valve positions can be optimized, such that the residence time and mass transfer rate of the phases in the extractor battery can be controlled, allowing for insulation against disturbances in feedstock concentration, which are inherent to many biodiesel processes that use waste oil from multiple sources.

The methods can function by arranging a battery of high-pressure mixing-settling vessels in countercurrent orientation. Liquid-liquid cyclone units are particularly well suited to the task, as they can produce separating force fields stronger than gravity and have conical shapes that withstand internal pressure well. Stronger force fields result in faster separation than simple settling. Even more conveniently, cyclonic units have internal asymmetric pressure gradients, allowing a single set of pumps to move two countercurrent streams along the battery.

Alternative extraction arrangements include liquid-contacting towers and traditional mixer settler units, which, while lacking some of the advantages of a cyclone battery, are more widely used for liquid-extracting operations and may be easier to use for process testing and optimization in the context of a pilot plant.

The methods provided herein can be used to separate biodiesel from a biodiesel and alcohol mixture in a variety of situations. In some embodiments, the concentration of biodiesel in the mixture prior to the separation is about 2 mol % to about 20 mol %. In some embodiments, the mixture is the product from a supercritical biodiesel production. The methods can be used to separate the biodiesel so that the alcohol can be reused, e.g. can be regenerated back into the biodiesel production. In some embodiments, when the biodiesel is extracted in a nonpolar phase during the extraction, the concentration of the biodiesel extracted in the nonpolar phase is about 1 mol % to about 40 mol %, about 1 mol % to about 30 mol %, about 5 mol % to about 30 mol %, or about 10 mol % to about 30 mol % after the extraction. In some embodiments, essentially all of the biodiesel is removed from the alcohol mixture using multi-stage extraction. For example, in some aspects the concentration of the biodiesel in the alcohol is about 5000 ppm, about 1000 ppm, about 500 ppm, about 250 ppm or less after the extraction.

Provided herein are methods that can include integration of the blending process with the fuel production process. Petrodiesel is primarily composed of nonpolar molecules such as long-chain alkanes, aromatics and cyclic alkanes. The weak polarity of methanol allows it to dissolve the locally-polar biodiesel molecules, but the strongly nonpolar petrodiesel is a far more effective biodiesel solvent. In various embodiments, methods of making a biodiesel blend are provided, the method can include extracting biodiesel from a mixture of biodiesel and alcohol using a multi-stage extraction method provided herein, wherein the biodiesel blend has a biodiesel content from about B2 to about B25, about B2 to about B20, about B2 to about B15, about B5 to about B15, about B5 to about B20, or about B2 to about B10.

This leaves the plant with about 90% of the recycled methanol still at 90 bar and a product that can be sold at retail price by the plant to consumers or at wholesale price to vendors as a B15 biofuel blend. With petrodiesel on hand for the extraction process, this product can also be further diluted to B2 to access a wider market of approved engine types.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

The premise of the design is based on a few fundamental scientific concepts. Of immediate economic interest is the principle that for a real fluid, specific enthalpy is a monotonic function during adiabatic compression. It takes work, that is, to increase the pressure of a fluid. For this reason, design was carried out with the goal of maintaining available pressure head in the process stream. More indirectly, the elimination of the need for a third party blender or an extra in-house blending process offers certain advantages in terms of capital investment, utility expenditure and product value.

The technical feasibility of the process was designed and simulated to meet the following design specifications.

| | |
|---|---|
| Desired Production of B15 (gallons/year) | 4,500,000 |
| Minimum Acceptable Methanol Recycle Pressure (bar) | 90 |
| Minimum Biodiesel Content (vol %) | 15 |
| Maximum Acceptable Biodiesel Loss (mol %) | 0.5 |

The influent stream on the left is supplied at the reactor temperature and pressure, while the influent on the left is supplied at 125 bar and near-ambient temperature. The pressure in each cyclone increases from left to right due to the induced pressure drop of the vortex, allowing the countercurrent flow of two fluids to be actualized with only a single system of pumps. The underflow will naturally flow in one direction, while the overflow is mechanically impelled in the opposite direction. This advantage is not available to traditional mixer-settler batteries, as differential pressures across the unit will impede settling due to backflow. Since internal pressure gradients are important to the operation of cyclone units, the plant only has to purchase and operate 12 pumps instead of 24.

It is advantageous to increase pressure sequentially in this fashion, as it reduces the compressive load on the methanol compressor down the line, supplying the feed at 89 bar instead of 77 bar. Applying mechanical suction from the overhead pipe also gives the operator more control over the internal velocity field than the alternative. Reducing the duty of an underflow pump to improve vortex integrity likely does not offer any additional functionality over that offered by a modular underflow aperture.

The incorporation of the blending process into the purification process offers technical advantages. Each cyclonic unit acts as a mixer-settler to remove methanol, which conveniently eliminates the need for agitated blending of the finished product. The blended fuel also has a longer shelf life than B100, making the storage, transport and sale of the product easier.

Moreover, the incorporation of the blending process is not only advantageous in itself, but essential to achieving the technical advantages offered by the extraction process. Without conventional diesel as a mass separating agent, methanol and biodiesel are miscible at 200 C until the pressure is reduced to 35 bar, at which point the first bubble of methanol vapor forms. Only at about 5 bar does 95% of the mixture exist in the vapor phase, approximating the state of acceptable methanol recovery.

The performance of the system was modeled using UNIFAC to model low-pressure nonideality for the ternary mixture. The Peng-Robinson equation of state was used to predict the ideal mixture phase behavior near the critical point. The Wong-Sandler mixing rules were used to improve predictive power of the Peng-Robinson equation of state for non-ideal mixtures at high pressures. The Wong-Sandler mixing rules were assumed to be pressure insensitive over the range of modelled pressures (1 to 125 bar). The properties of dodecane were used to represent the properties of a commercial diesel blend, whereas methyl laurate was used to simulate a chemical representation of a generic biodiesel mixture. The pumping and compression operations were treated as isentropic, and the reactor effluent was maintained at a 1:42 ratio of methyl esters to methanol without additional adulterants. The cyclone units were operated adiabatically and assumed to be near frictionless in the supercritical region. The spontaneous phase decomposition was treated as very fast compared to mechanical phase separation, and relative droplet wall velocity was slow compared to droplet angular velocity. The distribution constant $K'_{DB}$ was assumed to be independent of feed composition, temperature and pressure. The surface concentration of biodiesel in methanol was approximately zero after stage 1.

To predict the appearance of the two-phase liquid system, careful selection of thermodynamic simulation methods was used. The highly non-ideal liquid system required adaptations to the traditional activity model to incorporate the influence of pressure on intermolecular effects. At standard temperature and pressure, the UNIFAC model does a good job for predicting liquid systems. To this end, the ternary phase equilibrium of the system was modelled using UNIFAC parameters at 1 bar and 20° C.

Figure 7:
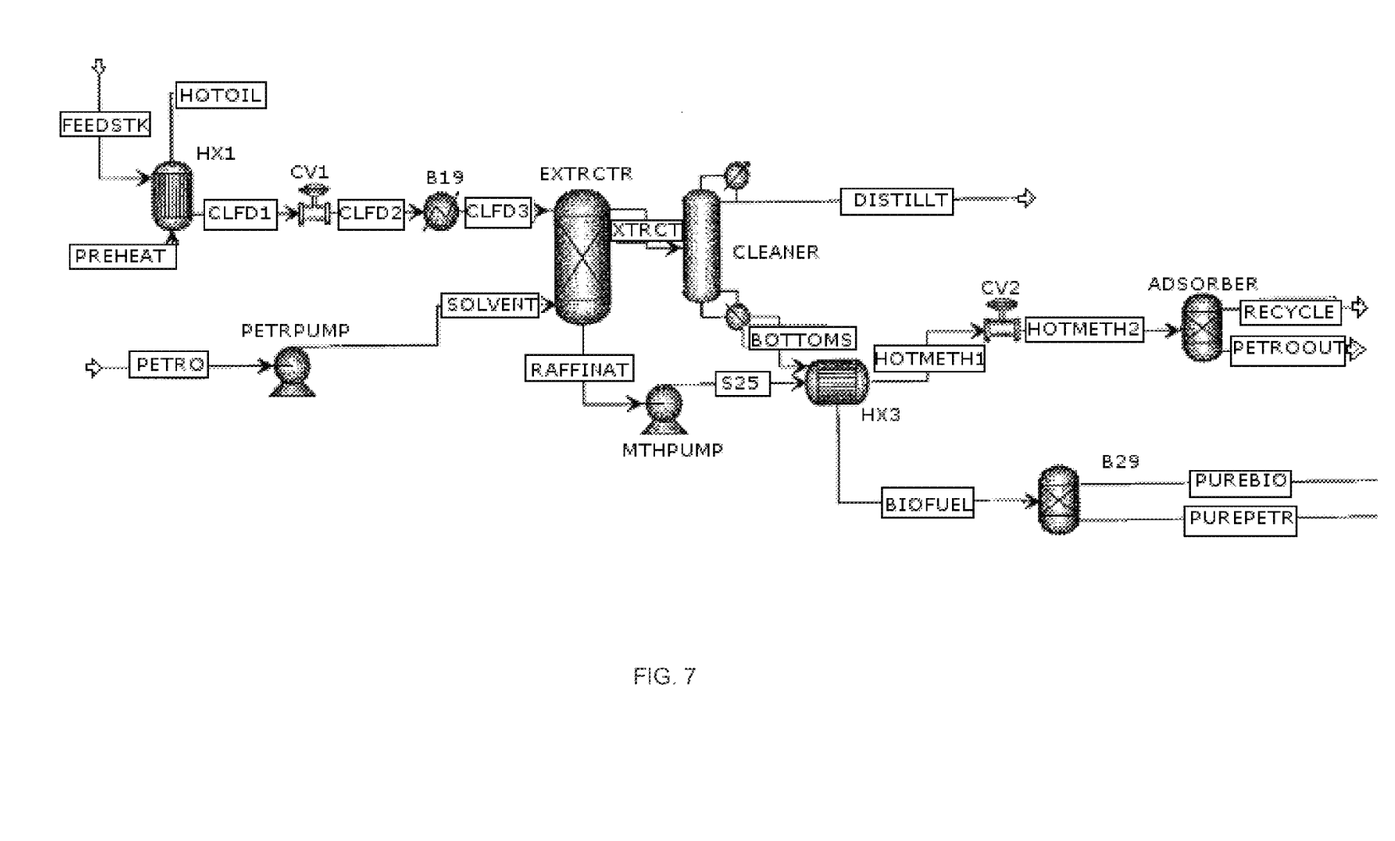
FIG. 7 is a generalized ASPEN flowsheet.

This data was then regressed in ASPEN to approximate the PRWS mixing rules. An ASPEN flowsheet is depicted in FIG. 7. These rules are believed viable at high pressures. Phase computations at 10° C. and 70 bar yielded a ternary phase diagram (FIG. 10) which agrees with the intermolecular affinities suggested in the introduction.

Figure 10:
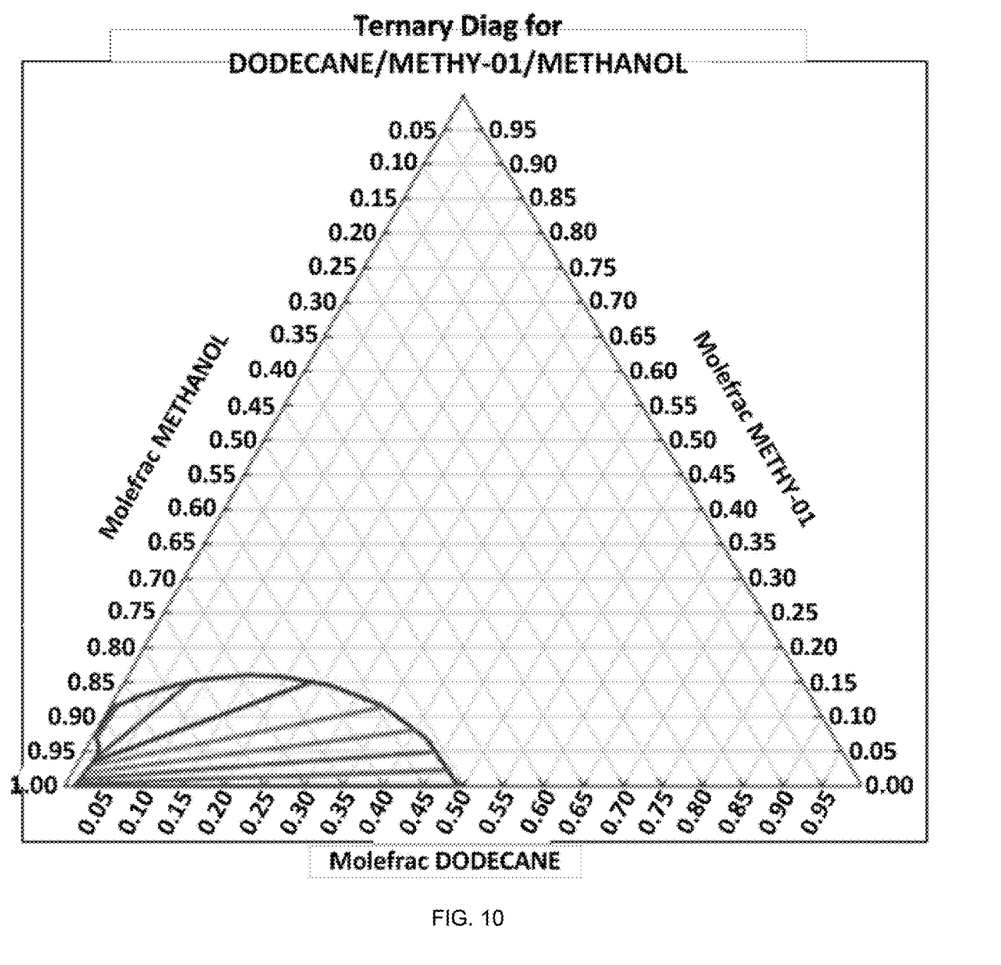
FIG. 10 is a ternary phase diagram for methanol, dodecane, and methyl laurate (methy-01) based on phase computations at 10° C. and 70 bar.

Indeed, at the limit of dodecane dilution, the unary-phase behavior is restored. At the limit of dodecane saturation, a single dodecane rich liquid phase occurs, as both solutes are miscible with conventional diesel at these conditions. Replicating these conditions is a challenge to be handled by carefully selecting, installing and optimizing the process equipment.

Up until methyl laurate mole fractions about 0.13, the slopes of the tie lines are quite similar. This allows the calculation of an extraction factor from the following equation.

$$E = K'_{DB} S / F_A$$

Wherein $K'_{DB}$ is the ratio of the ratio of the mass of biodiesel to petrodiesel in the extract phase to the ratio of the mass of biodiesel to methanol in the carrier phase at thermal equilibrium, approximated as constant from the appearance of the tie lines far from the plait point. S is the mass flow rate of pure dodecane into the extraction battery and $F_A$ is the rate of methanol mass flow from the reactor into the system.

Since one of those properties is a design variable, one is an assumption and the other is data immediately available from the preceding ternary phase diagram, the extraction factor E can be calculated and implemented in the equation for requisite countercurrent extraction stages.

$$\frac{X_B^R}{X_B^F} = \frac{E-1}{E^{N+1}-1}$$

The left denominator on the left hand side is the mass ratio of biodiesel to diesel in the extract. That value is computed by simply calculating the mass ratio of the biodiesel blend that the plant intends to sell. The numerator effectively expresses how much biodiesel remains in the recycle stream. That number is set to one half of a mass percent and the equation is solved for N, yielding the 12 cyclone battery outlined in the design premise above. Higher biodiesel recovery can be achieved by adding additional stages, though the return on capital investment in that regard will quickly diminish with\process extension, as pressure drop and pumping requirements will increase.

Thermodynamically, the maximum attainable mole percentage of methyl laurate is a little over fifteen percent. This occurs at the limit of infinite stages, but a more manageable obstacle to separation is that of mass transfer. Mass transfer to the expanding droplets of fluid is aided by convection, which is characterized by the relative velocity of a dispersed phase droplet to the continuous phase.

Earlier, one bar was selected as a pressure gradient across each unit. This is a design variable in the control of the plant designer, which can be tuned as needed to attain ideal performance. 12 bar of pressure drop across the whole cyclone battery is a generic value that can be easily scaled up or down. The actual internal velocity of the cyclone is governed both by pump duty and inlet diameter.

| | ASPEN Results Heat and Material Balance Table | | | | |
|---|---|---|---|---|---|
| Stream ID | | DILUANT | RXEFFLNT | HOTMETH | BIOFUEL |
| Temperature | C. | 20.0 | 330.0 | 330.0 | 212.1 |
| Pressure | bar | 1.000 | 125.000 | 125.000 | 1.000 |
| Vapor Frac | | 0.000 | 1.000 | 1.000 | 0.000 |

-continued

ASPEN Results
Heat and Material Balance Table

| Stream ID | | DILUANT | RXEFFLNT | HOTMETH | BIOFUEL |
|---|---|---|---|---|---|
| Mole Flow | kmol/hr | 6.634 | 42.879 | 32.688 | 7.144 |
| Mass Flow | kg/hr | 1130.000 | 1560.000 | 1047.689 | 1260.386 |
| Volume Flow | l/min | 24.889 | 199.155 | 157.128 | 34.022 |
| Enthalpy | Gcal/hr | −0.559 | −2.045 | −1.498 | −0.540 |
| Mole Flow | kmol/hr | | | | |
| DODECANE | | 6.634 | | | 6.116 |
| METHANOL | | | 41.859 | 32.686 | 0.009 |
| METHY-01 | | | 1.021 | 0.002 | 1.019 |
| WATER | | | | | |
| Mole Frac | | | | | |
| DODECANE | | 1.000 | | | 0.856 |
| METHANOL | | | 0.976 | 1.000 | 0.001 |
| METHY-01 | | | 0.024 | 52 PPM | 0.143 |
| WATER | | | | | |
| *** LIQUID PHASE *** | | | | | |
| Viscosity | cP | 3.341 | | | 0.265 |
| Surface Ten | dyne/cm | 25.385 | | | 9.902 |
| DMX | sqcm/sec | | | | |
| DODECANE | | 0.000 | | | <0.001 |
| METHANOL | | | | | <0.001 |
| METHY-01 | | | | | <0.001 |
| WATER | | | | | |

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

I claim:

1. A method of extracting biodiesel from a mixture of biodiesel and alcohol, the method comprising
    pumping the mixture into a first stage of a multi-stage liquid-liquid extraction apparatus having from 4 to 12 stages configured in a countercurrent or crosscurrent extraction arrangement with an operating pressure of about 80 bar to 140 bar and a pressure difference of from 0.5 bar to 5 bar applied across each stage,
    pumping a petrodiesel into a last stage of the multi-stage liquid-liquid extraction apparatus,
    removing a polar phase from the last stage of the multi-stage liquid-liquid extraction apparatus, wherein the polar phase comprises the alcohol, and
    removing a nonpolar phase from the first stage of the multi-stage liquid-liquid extraction apparatus, wherein the nonpolar phase comprises the petrodiesel and the biodiesel.

2. The method of claim 1, wherein the multi-stage liquid-liquid extraction apparatus comprises a plurality of stages configured in a crosscurrent extraction arrangement,
    wherein the method comprises pumping petrodiesel into each of the stages,
    wherein a two-phase system is formed in each stage, wherein the two-phase system includes a polar phase and a nonpolar phase,
    wherein the alcohol preferentially partitions into the polar phase and the petrodiesel and biodiesel preferentially partition into the nonpolar phase in each stage,
    wherein the method further comprises pumping the polar phase from each stage and into a next stage until exiting the last stage, and
    wherein the method further comprises removing the nonpolar phase from each stage to extract the biodiesel.

3. The method of claim 2, wherein the concentration of biodiesel in the mixture prior to the separation is about 2 mol % to about 20 mol %.

4. The method of claim 3, wherein the concentration of the biodiesel extracted in the nonpolar phase is about 5 mol % to about 30 mol % after the extraction.

5. The method of any claim 4, wherein the concentration of the biodiesel in the alcohol is about 500 ppm or less after the extraction.

6. The method of any claim 2, wherein the alcohol is selected from the group consisting of methanol, ethanol, 1-propanol, 2-propanol, 1-butanol, 2-ethoxyethanol, and a combination thereof.

7. The method of claim 1, wherein the multi-stage liquid-liquid extraction apparatus comprises a plurality of stages configured in a countercurrent extraction arrangement,
    wherein a two-phase system is formed in each stage, wherein the two-phase system includes a polar phase and a nonpolar phase,
    wherein the alcohol preferentially partitions into the polar phase and the petrodiesel and biodiesel preferentially partition into the nonpolar phase in each stage,
    wherein the method further comprises pumping the polar phase from each stage and into a next stage until exiting the last stage, and
    wherein the method further comprises pumping the nonpolar phase from each stage and into a preceding stage until exiting from the first stage to extract the biodiesel.

8. The method of claim 7, wherein the method is performed at a temperature from about 10° C. to about 150° C.

9. The method of claim 8, wherein the concentration of biodiesel in the mixture prior to the separation is about 2 mol % to about 20 mol %.

10. The method of claim 9, wherein the concentration of the biodiesel extracted in the nonpolar phase is about 5 mol % to about 30 mol % after the extraction.

11. The method of any claim 10, wherein the concentration of the biodiesel in the alcohol is about 500 ppm or less after the extraction.

12. The method of any claim 7, wherein the alcohol is selected from the group consisting of methanol, ethanol, 1-propanol, 2-propanol, 1-butanol, 2-ethoxyethanol, and a combination thereof.

13. A method of making a biodiesel blend, the method comprising extracting biodiesel from a mixture of biodiesel and alcohol using a petrodiesel,
    wherein the method is performed according to claim 1, and
    wherein the biodiesel blend has a biodiesel content from about B2 to about B25.

\* \* \* \* \*